United States Patent [19]
Zengel et al.

[11] 4,314,089
[45] Feb. 2, 1982

[54] PROCESS FOR THE PREPARATION OF NITROSOBENZENE

[75] Inventors: Hans Zengel, Kleinwallstadt; Manfred Bergfeld, Erlenbach; Werner Klostermeier, Klingenbeg, all of Fed. Rep. of Germany

[73] Assignee: Akzona Incorporated, Asheville, N.C.

[21] Appl. No.: 129,959

[22] Filed: Mar. 13, 1980

[30] Foreign Application Priority Data

Aug. 17, 1979 [DE] Fed. Rep. of Germany ....... 2933314

[51] Int. Cl.$^3$ .................... C07C 76/00; C07C 81/02
[52] U.S. Cl. .................................................. 568/949
[58] Field of Search ....................................... 568/949

[56] References Cited

U.S. PATENT DOCUMENTS

| 3,504,035 | 3/1970 | Polinski et al. | 568/949 |
| 3,578,720 | 5/1971 | Dodman et al. | 568/949 |
| 3,989,764 | 11/1976 | Woolley | 568/949 |
| 4,178,315 | 12/1979 | Zengel et al. | 568/949 |

Primary Examiner—Teddy S. Gron
Attorney, Agent, or Firm—Francis W. Young; Robert F. Green

[57] ABSTRACT

An improved process for the preparation of nitrosobenzene by catalytically reducing nitrobenzene with the use of a reducing agent selected from the group consisting of aliphatic compounds containing from about 1 to about 20 carbon atoms, cycloaliphatic compounds containing from about 4 to about 12 carbon atoms, benzene, naphthalene, and ethylenically unsaturated compounds containing from about 2 to about 10 carbon atoms is disclosed. The improvement comprises performing the reduction in the presence of from about 0.05 to about 4.0 moles of water per mole of nitrobenzene.

7 Claims, No Drawings

PROCESS FOR THE PREPARATION OF NITROSOBENZENE

BACKGROUND OF THE INVENTION

This invention relates to a process for the preparation of nitrosobenzene by catalytically reducing nitrobenzene.

A brief summary of processes for the production of nitrosobenzene may be found in U.S. Pat. No. 4,178,315 which specifically discloses a process for the preparation of nitrosobenzene by the catalytic reduction of nitrobenzene utilizing as a reducing agent a compound selected from the group consisting of aliphatic compounds containing from about 1 to about 20 carbon atoms, benzene, naphthalene, and ethylenically unsaturated compounds containing from about 2 to about 10 carbon atoms. In the process of said patent the catalyst which is utilized is preferably a mixture of manganese and lead oxides and the reduction is typically carried out at a temperature in the range from about 250° to about 450° C., in the presence of an inert gas such as carbon dioxide, nitrogen, or a noble gas. In the process the activity and selectivity, as well as the life of the catalyst may be increased substantially by subjecting it to a preliminary treatment with a hydrocarbon or hydrogen. Such a process, in which oxygen-free reducing agents instead of the previously customary oxygen-containing reducing agents, are used for the first time, was found to be superior to the known processes with respect to conversion level, selectivity, and catalyst service life. Therefore, a useful industrial process for the preparation of nitrosobenzene by the reduction of nitrobenzene has been provided through the invention in the aforementioned patent.

The object of the present invention is to further improve the process which is disclosed in U.S. Pat. No. 4,178,315.

SUMMARY OF THE INVENTION

Surprisingly, it has now been found that in the reduction of nitrobenzene, the addition of small quantities of water to the reduction mixture produces a considerable increase in the level of conversion. Therefore, the present invention provides an improved process for the preparation of nitrosobenzene by catalytically reducing nitrobenzene with the use of reducing agent selected from the group consisting of saturated aliphatic hydrocarbons containing from about 1 to about 20 carbon atoms, cycloaliphatic compounds containing from about 4 to about 12 carbon atoms, benzene, naphthalene, and ethylenically unsaturated compounds containing from about 2 to about 10 carbon atoms, wherein the improvement comprises performing the reduction in the presence of from about 0.05 to about 4.0 moles of water per mole of nitrobenzene.

DETAILED DESCRIPTION OF THE PREFERRED IMBODIMENT

As indicated, the improved process of the present invention involves the catalytic reduction of nitrobenzene with use of a specified reducing agent. The reduction is typically carried out at a temperature in the range from about 250° to about 450° C. and in the presence of an inert gas, such as carbon dioxide, nitrogen, or a noble gas.

Preferably, the activity and selectivity of the process, as well as the life of the catalyst may be increased substantially by subjecting the catalyst to a preliminary treatment with a hydrocarbon, or hydrogen.

In the process of the present invention the quantity of water utilized is from about 0.05 to about 4.0 moles per mole of nitrobenzene. Preferably, the water is present in an amount from about 0.1 to about 2.0 moles, per mole of nitrobenzene. It is surprising that such a small quantity of water, for example, as low as from about 0.05 to about 0.1 mole of water per mole of nitrobenzene, will produce a noticeable increase in conversion with constantly higher selectivity. Larger quantities than 4.0 moles of water per mole of nitrobenzene have no additional advantage with respect to conversion, and appear to impair the selectivity of the reaction, due to the formation of additional amine. Also, a larger throughput of water, which must be evaporated and subsequently condensed, is not advantageous for technical and economic reasons. Quantities of water less than about 0.05 mole, per mole of nitrobenzene, do not appear to produce any increase in reaction rate which is significant.

From U.S. Pat. No. 3,504,035, it is known that nitrobenzene in the gaseous phase can be reacted catalytically with low hydrocarbons, in the presence of water vapors, but the reaction discussed therein involves a reduction which proceeds selectively as far as the aniline stage. In the process the hydrocarbon in combination with the water vapor is reacted with the nitrobenzene at temperatures of about 500° C. and in the presence of a mixed hydrogenation-reforming catalyst. The reforming catalyst which is based on precious metal or nickel, iron, or chromium, causes the formation of hydrogen which with the support of the hydrogenation catalyst, for example, a copper catalyst, assists in the reduction of the nitro group to the amino group. In addition to the fact that the process in said patent leads to a different reaction product, the present process is based on an entirely different reaction mechanism. The present process proceeds at substantially lower temperatures and therefore does not contain a reforming process stage.

It must be considered surprising that under the conditions of the present process, especially in the absence of a reforming catalyst, the addition of water not only results in the reduction proceeding with high selectivity only as far as the stage of the desired nitrosobenzene, but, in comparision with the process of the aforementioned U.S. Pat. No. 4,178,315, it also results in an increase in the reaction rate.

The reducing agent preferably is selected from the group consisting of saturated aliphatic hydrocarbons containing from 1 to about 10 carbon atoms, ethylene, propylene, cycloaliphatic hydrocarbons containing from 4 to about 12 carbon atoms, benzene, and naphthalene. Thus the reducing agents may be, for example, methane, ethane, propane, butane, hexane, n-decane, cyclobutane, cyclopentane, cyclohexane, cycloheptane, cyclopentadiene, cycloheptane, and cyclohexadiene-1,3. Prefered hydrocarbons are methane, benzene, hexane, and benzine fractions with $C_4$ to $C_8$ hydrocarbons. The aromatic compounds, as discussed, are benzene and naphthalene. Their derivatives are, of course, included as useful reducing agents. Thus, the term benzene includes its derivatives, such as toluene ethylene benzene, isopropyl benzene and p-xylene and the term naphthalene includes it derivatives.

The catalysts which are useful are all known metal catalysts indicated to be useful in the process of the aforementioned U.S. Pat. No. 4,178,315. In this respect, one may also refer to German Pat. No. 1,810,828, British Pat. Nos. 1,322,531, 1,259,504, 1,251,836, and 1,251,844, Dutch Pat. No. 7,005,588, Japanese Pat. Nos. 47 31 937, 91 26 633, and German Pat. No. 2,346,388.

In the process of U.S. Pat. No. 4,178,315, the catalysts which are utilized are preferably the known manganese oxide/lead oxide catalysts. The catalysts consists of a mixture of manganese and lead oxide applied to a suitable carrier material such as pumice, aluminum oxide, activated carbon, asbestos, brick, or kieselguhr. The atomic ratio of manganese to lead may vary greatly, but in general it is in a range from about 20:1 to about 2:1. Preference is given to catalysts which contain manganese lead in a ratio of 2 atoms of manganese to one atom of lead. With respect to the preparation of the catalysts to be used in the process of the present invention, one may refer to the detailed statements relating thereto in the aforementioned U.S. patent.

As in the process of the aforementioned U.S. patent, the activity and selectivity, as well as the life of the catalyst may be substantially increased by means of a preliminary treatment of the catalyst by hydrocarbon or with hydrogen. The hydrocarbons which are useful in such a pre-treatment are the compounds already discussed and indicated to be useful as reducing agents. Preferably, the hydrocarbon to be used as the reducing agent is also used for the pre-treatment. The preliminary treatment is performed at a temperature of about 300° to about 400° C. and may last from about 0.5 to about 10 hours. It is advantageous to subject the catalyst to a preliminary treatment lasting for a period from about 0.5 to about 10 hours, preferably from about 1 to about 3 hours, in the absence of nitrobenzene, by heating the catalyst to temperatures from about 300° to about 400° C., in one of the hydrocarbons to be used as the reducing agent or in hydrogen.

The process of the present invention may be performed at a temperature from about 250° C. to about 450° C., preferably at a temperature from about 320° to about 410° C., all as specified in the aforementioned U.S. Pat. No. 4,178,315. It is therefore not very significant which catalyst and which hydrocarbon are used. In general, the process may be performed at atmospheric pressure, in the gas phase. For technical reasons it is often advantageous to work at somewhat higher pressure, as at pressures up to about 1.5 bar. However, it is possible to perform the conversion under much higher pressures up to about 15 bar, and therefore sometimes in the liquid phase. In the case of gas phase conversion, it has been found advantageous to make use of a diluent. Inert gases, such as carbon dioxide, nitrogen or the noble gases are suitable for such purpose.

The process of the present invention may be performed continuously, as well as discontinuously. For example, in the continuous operating method to be considered for an industrial-scale execution of the process, the nitrobenzene is evaporated, and preheated if required, heated to the reaction temperature together with the vaporous hydrocarbon, the water vapor and, if required, the inert gas, and then brought into contact with the catalyst. Advantageously the foregoing is performed in such a way that the gas mixture flows over, or through, catalyst bed in a tube reactor, either in a counter-current or in the same direction. Customary solid, or fluid bed, technology can be employed. The flow velocities of the gases are adapted to the desired contact times. In order to suppress continued reaction of the nitrosobenzene, use is made of contact times that are as short as possible and thus, in particular when fluid bed technology is used, of flow velocities that are high. In general, contact times are in a range from about 0.2 to about 40 seconds, preferably from about 0.5 to about 10 seconds.

Processing of the reaction mixture may be done in a simple manner, by quenching it after the catalyst. The water is thereby removed as a separate, liquid phase. It can thus be separated simply and re-used together with fresh water. Nitrosobenzene, unconverted nitrobenzene, as well as the by-products aniline, azo- and azoxybenzene are separated in the organic phase, from which the nitrosobenzene can be obtained by means of fractional distillation.

In the preliminary treatment of the catalyst it is expedient to proceed in such a way that the catalyst, after it has been dried, is transferred to the reactor, where it is treated at about 400° C. with one of the mentioned hydrocarbons or hydrogen for about 2 hours under exclusion of air, after which the nitrobenzene is supplied gradually. A gradual decline in catalyst activity, which can occur after a continuous operation lasting for weeks, may easily be reversed again by temporarily discontinuing the supply of nitrobenzene and water vapor during operation of the reactor, while maintaining the reaction temperature, so that the catalyst is in such a manner flushed for several hours with pure hydrocarbon, or hydrogen.

The present invention will be further described in the following and non-limiting examples.

EXAMPLE 1

(Preparation of Catalyst)

α-Aluminum oxide beads with a diameter of 0.8 to 1.2 mm were used as carrier for the catalyst. They were steeped in an aqueous solution of a mixture of lead and manganese nitrate (molar ratio Pb/Mn=1:2) and dried in a vacuum at 120° C. Subsequently, the catalyst was placed in the reactor and there treated with methane for 2 hours at 400° C.

EXAMPLE 2

A gas mixture, consisting of nitrobenzene, methane and water, preheated to 343° C., was conducted through a glass tube of about 50 cm length and an inside diameter of 1 cm, which contained 16 $cm^3$ of a Pb/Mn catalyst in the form of 1 mm beads, freshly prepared according to Example 1. The throughput amounted to 19.1 g/hr. (0.155 mol) of nitrobenzene, 40 Nlit/hr. (1.79 mol) of methane and 4 g/hr. (0.222 mol) of water. After leaving the reaction tube, which had been kept practically isothermally at 343° C. by means of electrical heating, the reaction mixture was quenched to room temperature in a water cooler and the constituents of low volatility were separated.

Under these conditions, a nitrobenzene conversion level of 23% was obtained after an hour, whereby nitrosobenzene was formed with 94% selectivity. The remaining 6% were composed of azoxybenzene, azobenzene and aniline.

EXAMPLE 3

(Comparison Example)

When the reaction was carried out under the same conditions as in Example 2, but without water in the stream of gas. the nitrobenzene conversion level was only 7%, while the selectivity remained equally high, namely 95%.

EXAMPLE 4

A gas mixture consisting of nitrobenzene, benzene, water and nitrogen was passed at 330° C. through the reactor described in Example 2. The throughput amounted to 18 g/hr. (0.146 mol) of nitrobenzene, 8 g/hr. (0.103 mol) benzene, 8 g/hr. (0.444 mol) of water and 50 Nlit/hr. (2.23 mol) of nitrogen. A conversion level of 17% nitrobenzene was reached after one hour, whereby nitrosobenzene was formed with 96% selectivity.

EXAMPLE 5

(Comparison Example)

When the reaction was carried out under the same conditions as in Example 4, but without water in the stream of gas, the level of nitrobenzene conversion was only 6%, whereby nitrosobenzene was formed with a selectivity of 96%.

EXAMPLES 6-9

380 cm$^3$ of a Pb/Mn catalyst freshly prepared according to Example 1, on 3 mm beads of $\alpha$-Al$_2$O$_3$ carrier, were placed in a stainless steel reactor of 465 cm length and an inside diameter of 33.5 mm. First, the catalyst was activated for 2 hours in a stream of methane at 400° C. Then, the temperature in the reactor was reduced to 300° C. and 135 g/hr. (1.1 mol) of nitrobenzene and 8 g/hr. (0.44 mol) of water were metered in at 300° C. via an evaporator.

By means of a circulating pump, 500 lit./hr. of gas were passed through the reactor and 32.5 Nlit/hr. (1.45 mol) of methane metered in via a mixing valve.

The gaseous reaction mixture was condensed in a cooler, drawn off continuously, and analyzed for nitrobenzene, nitrosobenzene, aniline, azo- and a azoxybenzene content.

Conversion level and selectivity, referred to nitrosobenzene, in dependence upon the reaction time, are compiled in the table.

| Example | Time (hr.) | Conversion (%) | Selectivity (%) |
|---------|------------|----------------|-----------------|
| 6 | 5 | 11.2 | 95 |
| 7 | 10 | 11.1 | 96 |
| 8 | 50 | 10.5 | 96 |
| 9 | 100 | 10.4 | 95 |

EXAMPLES 10-13

Using the reactor described for Examples 6-9, which was filled with 380 cm$^3$ of a freshly prepared Pb/Mn catalyst on 3 mm beads of an $\alpha$-Al$_2$O$_3$ carrier, nitrobenzene was converted to nitrosobenzene in the presence of different quantities of water. The reaction temperature was 320° C. The quantities metered in were 136 g/hr. (1.1 mol) of nitrobenzene and 500 lit/hr. of circulating gas, to which 32.5 Nlit/hr. (1.45 mol) of methane were added constantly.

Water was metered in as described for Examples 6-9. The gaseous reaction mixture was condensed and investigated for its content of nitro and nitrosobenzene, aniline, azo- and azoxybenzene.

The conversion and selectivity data, referred to nitrosobenzene, in dependence upon the admixture of water, are compiled in the table. For comparison purposes, Example 10 shows these data without the addition of water.

| Example | Addition of water g/hr. | mol/hr. | Conversion (5) | Selectivity (%) |
|---------|------|------|------|------|
| 10(comp.) | 0 | 0 | 10 | 95 |
| 11 | 2 | 0.11 | 14 | 95 |
| 12 | 20 | 1.11 | 16 | 94 |
| 13 | 80 | 4.44 | 18 | 92 |

What is claimed is:

1. An improved process selectively preparing nitrosobenzene by catalytically reducing nitrobenzene with a reducing agent selected from the group consisting of saturated aliphatic hydrocarbons containing from about 1 to about 20 carbon atoms, cycloaliphatic compounds containing from about 4 to about 12 carbon atoms, benzene, naphthalene, and ethylenically unsaturated compounds containing from about 2 to about 10 carbon atoms, wherein the improvement comprises adding to the reaction mixture from about 0.05 to about 4.0 moles of water per mole of nitrobenzene preliminary to the selective catalytic reduction.

2. The process of claim 1 wherein the reduction is performed at a temperature in the range from about 250° to about 450° C. and in the presence of an inert gas.

3. The process of claim 2 wherein the inert gas is carbon dioxide, nitrogen or a noble gas.

4. The process of claim 1, 2, or 3 wherein the quantity of water utilized is from about 0.1 to about 2.0 moles per mole of nitrobenzene.

5. The process of claim 4 wherein the reducing agent is selected from the group consisting of methane, ethane, propane, butane, hexane, n-decane, cyclobutane, cyclopentane, cyclohexane, cycloheptane, cyclopentadiene, cyclohexadiene-1,3, benzene, and benzine fractions with C$_4$ to C$_8$ hydrocarbons.

6. The process of claim 5 wherein the catalyst is a manganese oxide/lead oxide catalyst.

7. The process of claim 6 wherein the catalyst has been subjected to a preliminary treatment by heating it for 0.5 to 10 hours in one of the reducing agents, or in hydrogen, at temperatures from 300° to 400° C., in the absence of nitrobenzene.

* * * * *